US010948474B2

(12) United States Patent
Cui et al.

(10) Patent No.: US 10,948,474 B2
(45) Date of Patent: Mar. 16, 2021

(54) SIMULATION DEVICE AND METHOD FOR STUDYING THE INFLUENCE OF WETLAND PLANT LITTER DECOMPOSITION ON WATER QUALITY

(71) Applicant: Research Institute of Forestry New Technology, Chi, Beijing (CN)

(72) Inventors: Lijuan Cui, Beijing (CN); Yunmei Ping, Beijing (CN); Wei Li, Beijing (CN); Xu Pan, Beijing (CN); Manyin Zhang, Beijing (CN); Ziliang Guo, Beijing (CN); Changjun Gao, Beijing (CN); Yinuo Zhu, Beijing (CN)

(73) Assignee: RESEARCH INSTITUTE OF FORESTRY NEW TECHNOLOGY, CHINESE ACADEMY OF FORESTRY, Beijing (CN)

( * ) Notice: Subject to any disclaimer, the term of this patent is extended or adjusted under 35 U.S.C. 154(b) by 209 days.

(21) Appl. No.: 16/240,987

(22) Filed: Jan. 7, 2019

(65) Prior Publication Data

US 2019/0234927 A1    Aug. 1, 2019

(30) Foreign Application Priority Data

Jan. 26, 2018    (CN) .......................... 201810077953.6

(51) Int. Cl.
*G01N 33/18*    (2006.01)
*G01N 33/00*    (2006.01)
(Continued)

(52) U.S. Cl.
CPC .......... *G01N 33/186* (2013.01); *C02F 3/006* (2013.01); *C02F 3/32* (2013.01); *C02F 3/327* (2013.01);
(Continued)

(58) Field of Classification Search
CPC ............ G01N 33/186; G01N 33/0098; G01N 33/1806; C02F 3/006; C02F 2303/20; C02F 2301/02; Y02W 10/10; Y02A 40/22
See application file for complete search history.

(56) References Cited

U.S. PATENT DOCUMENTS

| | | | |
|---|---|---|---|
| 6,415,549 B1 * | 7/2002 | Beeson, Jr. .......... | A01G 9/0295 47/84 |
| 8,234,814 B2 * | 8/2012 | Kertz ..................... | A01G 9/024 47/67 |
| 2003/0150394 A1 * | 8/2003 | Wolfe ................... | A01K 63/042 119/246 |

* cited by examiner

*Primary Examiner* — Brandi N Hopkins
(74) *Attorney, Agent, or Firm* — Stuart H. Mayer; Mayer & Williams PC

(57) ABSTRACT

The invention "simulation device and method for studying the influence of wetland plant litter decomposition on water quality", belongs to the ecological engineering field. The simulation device comprises a distributing reservoir, a planting pool and a discharge bay, and the three are connected successively through a first-level pipeline; the distributing reservoir is used to supply water to the planting pool; the discharge bay is used to collect wastewater discharged from the planting pool; the planting pool comprises a plurality of planting units; the planting unit is a container-like structure and used to hold the planting substrate and plant wetland plants on the planting substrate. By using the simulation device and/or simulation method of the invention, the whole process of the influence of plant litters especially wetland plants litters on water quality under natural state can be highly simulated and restored.

13 Claims, 2 Drawing Sheets

(51) Int. Cl.
  *C02F 3/00* (2006.01)
  *C02F 3/32* (2006.01)
  *C02F 103/00* (2006.01)
  *C02F 101/30* (2006.01)
(52) U.S. Cl.
  CPC ..... *G01N 33/0098* (2013.01); *G01N 33/1806* (2013.01); *G01N 33/1826* (2013.01); *C02F 2101/30* (2013.01); *C02F 2103/007* (2013.01); *C02F 2201/005* (2013.01); *C02F 2201/007* (2013.01); *C02F 2301/02* (2013.01); *C02F 2303/20* (2013.01); *Y02A 40/22* (2018.01)

SIMULATION DEVICE AND METHOD FOR STUDYING THE INFLUENCE OF WETLAND PLANT LITTER DECOMPOSITION ON WATER QUALITY

TECHNOLOGY FIELD

The invention belongs to the field of ecological engineering technology, and relates to a simulation device and method for studying the influence of wetland plant litter decomposition on water quality.

BACKGROUND TECHNOLOGY

Wetland plants play an important role in sewage purification and other aspects. There are many kinds of wetland plants and they have strong regional characteristics. There are large differences among different wetland plants in the ability to remove pollutants. However, a large number of wetland plants will cause more plant litter inevitably. Therefore, screening plant litter with faster decomposition rate and poor pollution ability has important theoretical and practical significance for wetland water quality purification and water environment restoration. There have been many reports on the study of using wetland plants such as *Phragmites communis*, *Typha orientalis* and *Zizania latifolia* to construct constructed wetlands to treat sewage by scholars at home and abroad. Wetland plants play an important role in constructed wetlands. However, there are few reports on how these plant litters are treated and what impact they will have on water quality.

It's shown by researches on litter decomposition of wetland emergent plants that, different decomposition rates of wetland plant litter have different impacts on water body. However, the decomposition of emergent plants is mostly decomposition after plants lodging, and there are few studies on the standing decomposition of emergent plants as well as the difference between lodging decomposition and standing decomposition, Which kind of emergent plant litter will have a greater impact on the water body, and that the mixed decomposition of plant litter will aggravate or reduce the second level pollution to the water quality need to be further verified. The main wetland emergent plants studied at home and abroad are *Phragmites communis*, *Typha orientalis*, *Oryza sativa*, silvergrass, *Zizania latifolia*, sparganium, scirpus tabernaemontani, juncus effusus, water-garden Iris, arrowhead, rhizoma alismatis, acorns calamus, etc.

At present, the research on sewage purification efficiency of wetland plant mainly focuses on small indoor area research, and the research device is usually an independent closed container. As to every wetland plant grown in each container, except litter, other factors that may affect the changes of water quality indicators are uncontrollable. It is impossible to restore the situation that litter in the natural state fall into the water body and thus affect the water quality.

Therefore, there is an urgent need to develop a simulation device and method to highly simulate and restore the influences of wetland plant litter on water quality under natural conditions, which can be used to study the influences of wetland plant litter on water quality.

SUMMARY OF THE INVENTION

Based on above gaps and urgent needs in the field, the present invention aims to provide a purification functional simulation device of wetland emergent plant standing litter and method to apply such simulation device to remove wetland plant litter.

The technical solution of the invention is as follows:

Simulation device for studying the influence of decomposition of plant litter on water quality, characterized in that, comprising a distributing reservoir, a planting pool and a discharge bay, and the three parts are connected successively through a first-level pipeline; the distributing reservoir is used for supplying water to the planting pool; the discharge bay is used for collecting waste water discharged from the planting pool; the planting pool comprises at least 1 planting unit; the planting unit is a container-like structure and used to hold the planting substrate and plant the plant on the planting substrate.

The planting pool comprises a plurality of planting units; the plurality of planting units are arranged in parallel arrangement, so that the water flowing out of the distributing reservoir can enter each planting unit respectively, and the wastewater in each planting unit can flow out separately and enter the discharge bay.

The plurality of planting units are arranged in an array along the first-level pipeline arrangement direction; the planting pool includes at least 1 array; inside the array, each planting unit through respective second level pipelines connecting with the first-level pipelines leading from the distributing reservoir to form the parallel arrangement.

The planting pool comprises two of said arrays; according to the direction of water flow, the first-level inlet pipelines of the two branches formed by the left and right branches of the first-level pipeline from the distributing reservoir enter the upstream part of the two arrays respectively, and the first-level outlet pipelines of the two branches leading from the downstream part of the two arrays rejoin to form a first-level outlet pipeline which is connected to the discharge bay, in order to form the parallel arrangement.

According to the direction of water flow, the first-level pipeline leading from the distributing reservoir to the planting pool is a first-level inlet pipeline, the pipeline leading from the planting pool to the discharge bay is a first-level outlet pipeline; each planting unit has a water inlet and a water outlet, and the water outlet of each planting unit is respectively connected to the first-level outlet pipeline through a second level outlet pipeline, and the water inlet of each planting unit is connected to the first-level inlet pipeline through a second level inlet pipeline, so that the respective planting units are arranged in the parallel arrangement.

The first-level pipeline and the second level pipeline are provided with on-off valves for controlling water in and out; the diameter of the first-level pipeline is larger than the diameter of the second level pipeline.

Preferably, both of the second level pipeline and the second level pipeline on the upstream and downstream part of the planting pool of the simulation device are provided with on-off valves.

More preferably, an on-off valves is arranged on the location of the first level pipeline leading from the distributing reservoir of the simulation device which is near the water outlet of the distributing reservoir.

The water inlet of the planting unit is parallel to or higher than the water outlet; the water outlet of the planting unit is disposed at a position parallel to or slightly lower than the upper surface of the planting substrate in the planting unit.

A baffle is vertically disposed in the planting unit for preventing plants in the planting unit from falling down.

The plant is a wetland plant; the planting substrate in the planting unit is a substrate suitable for the growth of the plant.

A simulation method for studying the influence of plant litter decomposition on water quality, characterized in that, the plant is planted in the planting unit of the planting pool of the simulation device.

After the plant is planted in the planting unit, the water in the distributing reservoir is discharged into the planting pool by controlling the flow of the water body by controlling the on-off valves, and after a period of time, the indicator changes of the water after decomposition of the plant litter in the planting pool are measured.

The plant is a wetland plant; different or identical wetland plants are planted between each planting unit.

In one aspect, the present invention provides a simulation device for studying the influence of plant litter decomposition on water quality. The simulation device comprises a distributing reservoir, a planting pool and an discharge bay, and the three are connected in sequence through the first-level pipelines. The distributing reservoir is used to supply water to the planting pool. The discharge bay is configured to collect wastewater discharged from the planting pool. The planting pool comprises at least one planting unit. The planting unit is a container-like structure for containing the planting substrate and planting wetland plants on the planting substrate. The simulation device of the present invention can be used for the study of the influence of litter of wetland plants, aquatic plants and the like on water quality, and is not limited to wetland plant litter. The invention mainly aims at the characteristics of the environment where the litter of the wetland plant is located, including the inflow, the stay and the outflow of the water body, and the invention can highly simulate and restore the change of the water quality of the water caused by the plant litter entering the water body under the natural state.

Preferably, the planting pool comprises a plurality of planting units. The plurality of planting units are arranged in parallel arrangement, so that the water flowing out of the distributing reservoir can enter each planting unit respectively, and the wastewater in each planting unit can flow out separately and enter the discharge bay. The parallel arrangement prevents the water in the previous planting pool from affecting the water body of the next planting pool. In the case of series connection, the water body will enter in sequence, and the wastewater from the front unit will enter the rear unit and affect the water body index data of the rear unit. In this arrangement, there is no problem that the water sequentially pass through the planting pools in sequence when the planting pools are connected in series, thereby avoiding the problem that the latter planting unit is affected by the previous planting unit. Parallel arrangement can ensure that the water quality of the influent of each planting pool is the same, and each planting unit is not affected by each other, but at the same time, the water source flowing into each planting unit can be ensured to be the same, so as to minimize the influencing factors other than litter, and can highly restore the influences of wetland plant litter on water quality under natural conditions.

Further preferably, the plurality of planting units are arranged in an array along the first-level pipeline arrangement direction; the planting pool includes at least 1 array; inside the array, each planting unit through respective second level pipelines connecting with the first-level pipeline from the distributing reservoir to form the parallel arrangement. The array can better simulate the community state of wetland plant, thereby better restore the impact of actual decomposing process of wetland plant on water quality.

More preferably, the planting pool comprises 2 arrays; according to the direction of water flow, the first-level inlet pipelines of the two branches formed by the left and right branches of the first-level pipeline from the distributing reservoir enter the upstream part of the two arrays respectively, and the first-level outlet pipelines of the two branches leading from the downstream part of the two arrays rejoin to form a first-level outlet pipeline which is connected to the discharge bay, in order to form the parallel arrangement.

Further, the simulation device also has the following features: according to the direction of water flow, the first-level pipeline leading from the distributing reservoir to the planting pool is a first-level water inlet pipeline. The pipeline leading from the planting pool to the discharge bay is a first-level water outlet pipeline. Each planting unit has a water inlet and a water outlet, and the water outlet of each planting unit is respectively connected to the first-level water outlet pipeline through a second level water outlet pipeline, and the water inlet of each planting unit is connected to the first-level inlet pipeline through a second level inlet pipeline, so that the respective planting units are arranged in the parallel arrangement. Parallel arrangement can ensure that the water quality of the influent of each planting pool is the same, and each planting unit is not affected by each other. This arrangement avoids the problem that the water bodies are sequentially passed through the planting pools in sequence when the planting pools are connected in series, thereby causing that the latter planting pool is affected by the previous planting pool.

In some examples, both of the first-level pipeline and the second level pipeline are provided with an on-off valves for controlling the ingress and egress of water. The first-level pipeline includes a first-level inlet pipeline and a first level outlet pipeline, and similarly, the second level pipeline includes a second level inlet pipeline and a second level outlet pipeline. The diameter of the first-level pipeline is larger than that of the second level pipeline, so that the water flow of the first-level pipeline is greater than that of the second level pipeline.

In some preferred solutions of this group of examples of the present invention, the water inlet of the planting unit is parallel to or higher than the water outlet; the water outlet of the planting unit is disposed at a position parallel to or slightly lower than the upper surface of the planting substrate in the planting unit, the goal of this setting is to facilitate the thorough clearing of the water in the planting pool without affecting the next water inlet.

In other examples of the group, the planting unit is vertically provided with a baffle plate for preventing the plants in the planting unit from lodging. The role of the baffle is to assist the plant litter in the state of standing; the position of the baffle is above the water surface without affecting the flow of water. If the collected plant litter can be erected in the substrate, the baffle can be removed; the number of baffles is not clearly limited when ifs required to place the baffle.

In some specific examples of the group, the plant is a wetland plant. The planting substrate in the planting unit is suitable for the growth of the plant. More specifically, the planting substrate in the planting unit may comprise a multi-layered substrate, for example, a multi-layered substrate of a block stone layer, a gravel layer and a loam layer from top to bottom respectively. The planting substrate can also be other forms, and the substrate that is closer to the natural characteristics of the wetland is selected and formulated as much as possible. According to different plant objects that are actually studied, a person skilled in the art can place different substrates close to the natural state and suitable for various plant growth in the planting unit.

As used herein, "wetland plants" refer to plants grown in an excessive humid environment. Further, the wetland plants refer to plants that grow at junction between water and land, where the soil is wet or where there is shallow ponding environment. There are many kinds of wetland plants, including aquatic, helophyte, halophytic and some mesophytes (for example, mesophytic herbage).

Based on any of the above simulation devices, in another aspect, the present invention provides a simulation method for studying the influence of plant litter decomposition on water quality. The simulation method is characterized in that the plant to be studied is planted in the planting unit of the planting pool of the simulation device by using the simulation device.

Further, after the plant is planted in the planting unit, the water in the distributing reservoir is discharged into the planting pool by controlling the flow of the water body by controlling the on-off valves, after a period of time, the indicator changes of the water after decomposition of the plant litter in the planting pool are measured.

Further, the plant is a wetland plant; each planting unit is planted with different or the same wetland plants respectively.

In order to accomplish the object of the present invention, a purification functional wetland plant simulation device of the invention comprises a distributing reservoir, a planting pool and a discharge bay, the distributing reservoir and the discharge bay are respectively connected to the planting pool through pipelines. Wherein, the pipeline connected to the distributing reservoir, the planting pool or the discharge bay is provided with an on-off valves for controlling the ingress and egress of water. The planting pool is paved with block stone, gravel and loam from top to bottom.

The object of the present invention is to simulate the complete process of wetland plant falling by the simulation device, and through the experimental results of the simulation process, the influence of different plant litters on the water body under the same external conditions, whether the influence is big or small, good or bad can be obtained. It is also possible to obtain the influence of different states (standing and lodging) of the same plant litter on the water body.

In addition, the simulation device of the present invention can also be used to flexibly design experiments according to different experimental purposes. According to the experiment result of the influence of the litter on water quality, the simulation device can be further applied to the wetland simulation management under natural conditions. When wetland plants enter the death stage, a large number of plant litters begin to decompose, which may affect the water body. In order to reduce the influence of decomposition on the water body, operators can adopt the way to remove litters from the wetland. In this way, when the litters are removed, the litters in each planting unit can be sequentially removed according to the results obtained by the experiment of the influence of the litter on the water quality.

When using the simulation device to carry out experiment, at the end of the experiment, if the plant litters placed still exist and are not needed, the operator can manually clean the litters out of the device, and if the plant litters are completely decomposed, there is no need to clean them. Due to the complete simulation device of the present invention can highly simulate and restore the entire process of the influence of plant litters, especially wetland plant litters on water quality, in addition to being used for studying the influence of litter on water quality, the device of the present invention can be further used to sequentially remove the plant litters in the wetland water body according to the experimental result, thereby achieving the purpose of reducing polluted water.

The number signs in above figures are listed below: 1—distributing reservoir; 2—planting pool; 21—planting unit; 211—planting substrate; 212—baffle; 213—water body; 3—discharge bay; 4—first-level pipeline; 41—first-level inlet pipeline; 42—first-level outlet pipeline; 5—second level pipeline; 51—second level inlet pipeline; 52—second level outlet pipeline.

EMBODIMENTS

The content of the present invention is further described in detail through the following specific examples with reference to the accompanying drawings, but without limiting the scope of the invention. The consumables used in the following examples are commercially available unless otherwise stated. The operation steps are normal operations which is understood by a person skilled in the art unless otherwise stated.

Examples Group 1, Simulation Device of the Present Invention

This group of examples provides a simulation device for wetland plant litter. In all examples of the group, the simulation device has the following features: comprising a distributing reservoir, a planting pool and a discharge bay, and the three parts are connected successively through a first-level pipeline; the distributing reservoir is used for supplying water to the planting pool; the discharge bay is used for collecting waste water discharged from the planting pool; the planting pool comprises at least 1 planting unit; the planting unit is a container-like structure and used to hold the planting substrate and plant the plant on the planting substrate. The simulation device of the present invention can be used for the study of the influence of litters of wetland plants, aquatic plants and the like on water quality, and is not limited to wetland plant litters. The invention mainly aims at the characteristics of the environment where the litter of the wetland plant is located, including the inflow, the stay and the outflow of the water body, and the invention can highly simulate and restore the change of the water quality of the water caused by the plant litter entering the water body under the natural state.

Figure 1:
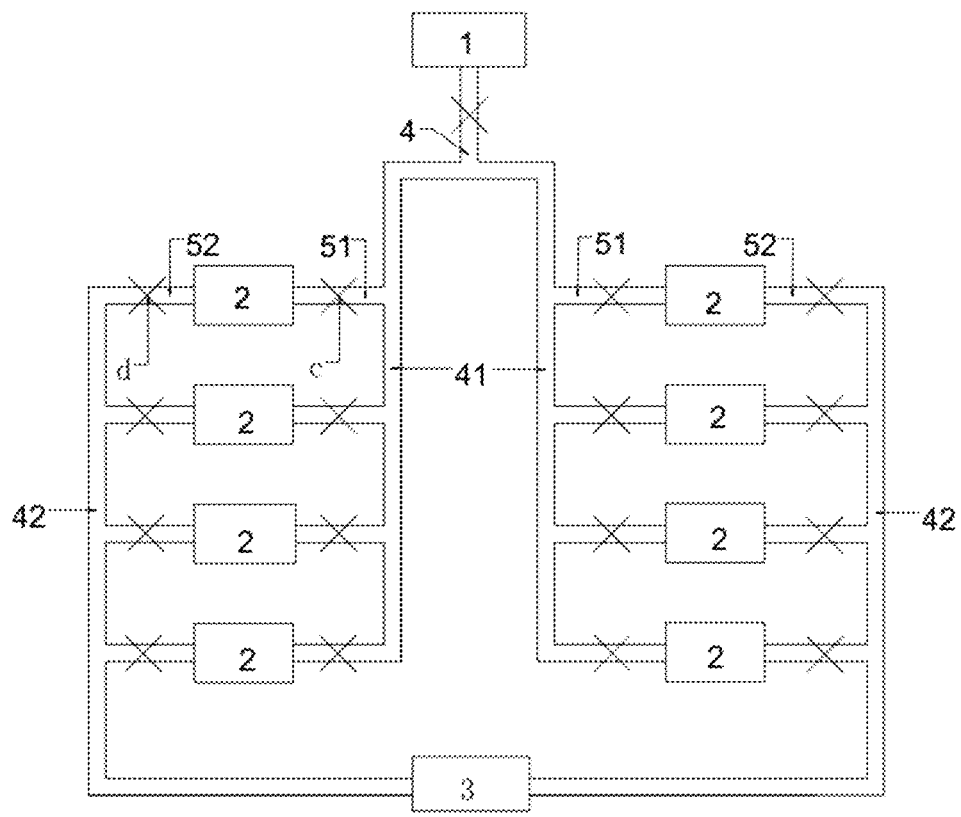
FIG. 1 is a plane structure schematic diagram of the simulation device of an example of the invention.

In preferred examples, as shown in FIG. 1, the planting pool comprises a plurality of planting units 21; the plurality of planting units 21 are arranged in parallel arrangement, so that the water flowing out of the distributing reservoir 1 can enter each planting unit 21 respectively, and the wastewater in each planting unit 21 can flow out separately and enter the discharge bay 3. The parallel arrangement prevents the water in the previous planting unit of the planting pond 2 from affecting the water body of the next planting unit 21. In the case of series connection, the water body will enter in sequence, and the wastewater from the front unit will enter the rear unit and affect the water body index data of the rear unit. This arrangement avoids problem that the water bodies are sequentially passed through the planting pools in sequence when the planting units are connected in series, thereby avoiding the problem that the latter planting unit is affected by the previous planting unit. Parallel arrangement can ensure that the water quality of each planting unit in the planting pool is the same, and each planting unit is not affected by each other, but at the same time, the water source flowing into each planting unit can be ensured to be the same, so as to minimize the influencing factors other than litter, and can highly restore the influences of wetland plant litter on water quality under natural conditions.

In further preferred examples, as shown in FIG. 1, the plurality of planting units 21 are arranged in an array along the first-level pipeline 4 arrangement direction; the planting pool 2 includes at least 1 array; inside the array, each planting unit 21 through respective second level pipelines 5 connecting with the first-level pipeline 4 from the distributing reservoir 1 to form the parallel arrangement.

In more preferred examples, as shown in FIG. 1, the planting pool 2 comprises 2 arrays; according to the direction of water flow, the first-level inlet pipelines 41 of the two branches formed by the left and right branches of the first-level pipeline 4 from the distributing reservoir 1 enter the upstream part of the two arrays respectively, and the first-level outlet pipelines 42 of the two branches leading from the downstream part of the two arrays rejoin to form a first-level outlet pipeline 42 which is connected to the discharge bay 3, in order to form the parallel arrangement.

In further examples, the simulation device also has the following features: according to the direction of the water flow, the first-level pipeline 4 leading from the distributing reservoir 1 to the planting pool 2 is a first-level water inlet pipeline 41. The pipeline leading from the planting pool 2 to the discharge bay 3 is a first-level water outlet pipeline 42. Each planting unit 21 has a water inlet and a water outlet, and the water outlet of each planting unit 21 is respectively connected to the first-level water outlet pipeline through a second level water outlet pipeline, and the water inlet of each planting unit is connected to the first-level inlet pipeline 41 through a second level inlet pipeline 51, so that the respective planting units 21 are arranged in the parallel arrangement. Parallel arrangement can ensure that the water quality of the influent of each planting pool is the same, and each planting unit is not affected by each other. This arrangement avoids the problem that the water bodies are sequentially passed through the planting pools in sequence when the planting pools are connected in series, thereby causing that the latter planting pool is affected by the previous planting pool.

In some examples, both of the first-level pipeline 4 and the second level pipeline 5 are provided with an on-off valves for controlling the ingress and egress of water. The first-level pipeline 4 includes a first-level water inlet pipeline 41 and a first-level water outlet pipeline 42, and similarly, the second level pipeline 5 includes a second level water inlet pipeline 51 and a second level water outlet pipeline 52. The diameter of the first-level pipeline 4 is larger than the diameter of the second level pipeline 5.

In some preferred solutions of this group of examples of the present invention, the water inlet of the planting unit 21 is parallel to or higher than the water outlet; the water outlet of the planting unit 21 is disposed at a position parallel to or slightly lower than the upper surface of the planting substrate in the planting unit, the goal of this setting is to facilitate the complete clearing of the water in the planting pool without affecting the next water inlet.

In other examples of the group, the planting unit is vertically provided with a baffle plate for preventing the plants in the planting unit from lodging. The role of the baffle is to assist the plant litter in the state of standing, the position of the baffle is above the water surface without affecting the flow of water. If the collected plant litter can be erected in the substrate, the baffle can be removed; the number of baffles is not clearly limited when ifs required to place the baffle.

In some specific examples of the group, the plant is a wetland plant; the planting substrate in the planting unit is suitable for growth of the plant. More specifically, the planting substrate in the planting unit may comprise a multi-layered substrate, for example, a multi-layered substrate of a block stone layer, a gravel layer and a loam layer from top to bottom respectively. The planting substrate can also be other forms, and that is closer to the natural characteristics of the wetland is selected and formulated as much as possible. According to different plant objects that are actually studied, a person skilled in the art can place different substrates close to the natural state and suitable for various plant growth in the planting unit.

As used herein, "wetland plants" refer to plants grown in an excessive humid environment. Further, the wetland plants refer to plants that grow at junction between water and land, where the soil is wet or where there is shallow ponding environment. There are many kinds of wetland plants, including aquatic, helophyte, halophytic and some mesophytes (for example, mesophytic herbage).

Examples Group 2, Simulation Method of the Present Invention

This group of examples provides a simulation method for studying the influence of plant litter decomposition on water quality based on the simulation device provided by any example of examples group 1. All the examples of this group have the following features: the plant to be studied is planted in the planting unit of the planting pool of the simulation device using the simulation device provided by any solution of examples group 1.

In further solutions of this group of examples, after the plant is planted in the planting unit, the water in the distributing reservoir is discharged into the planting pool by controlling the flow of the water body by controlling the on-off valves. After a period of time, the indicator changes of the water after decomposition of the plant litter in the planting pool are measured.

In more specific examples, the water inflow of a single planting pool can be controlled according to the wetland plant type in the planting pool. More specifically, the water level in the planting pool is controlled by controlling the on-off valves, and then to control the water inflow in the planting pool, so that the amount of water in each planting pool can be adapted to the plant type and plant litter type in the planting pool.

Generally speaking, the water inflow of a single planting pool can be in accordance with the actual inflow of constructed wetland, and the amount of discharged water of the distributing reservoir is the sum of the water amount of all the planting pools.

The water inflow of planting pool can be controlled according to the wetland plants of different life forms The water inflow of emergent plant may be larger and that of submerged plant may be smaller, but they can be the same. For the planting pool with large water volume, the litters may decay more seriously and decompose faster under the same decomposition time.

In further solutions of this group of examples, the plant is a wetland plant; each planting unit is planted with different or the same wetland plants respectively.

The simulation method also includes the mixed decomposition of two or more plant litters by the mixed decomposition of the same or different plant litters. By detecting the change of water quality, the influence of litter decomposition on the water body is judged.

Plant litters under different conditions (standing and lodging) have different influences on water quality. Generally speaking, the decomposition of lodging plants may have a greater impact on water quality than that of standing plants. Because their contact area with water is larger, it may accelerate their decomposition.

Figure 2:
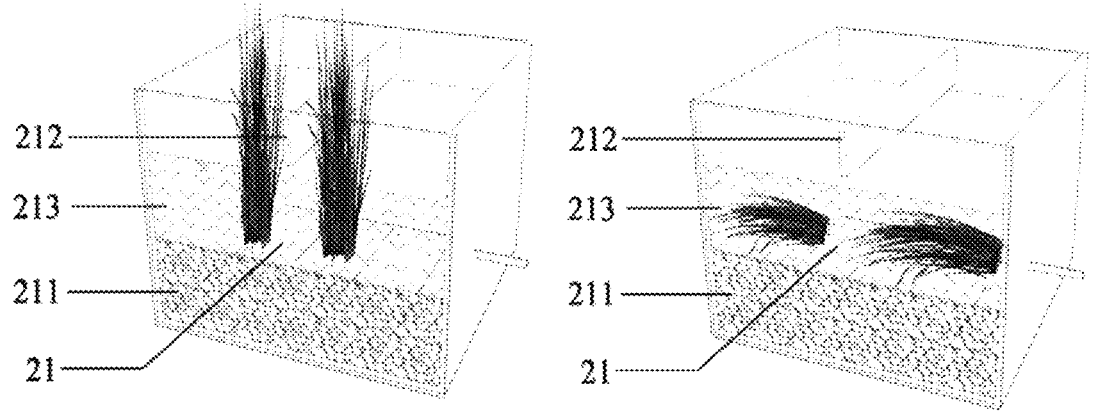
FIG. 2 is a structure schematic diagram of the planting unit of the simulation device of an example of the invention. It's shown by the comparison of left and right diagrams in the figure that the simulation device of the present invention can compare the decomposition of different states (standing and lodging) of the same plant, to compare the difference of influence on water body under two states.
Figure 3:
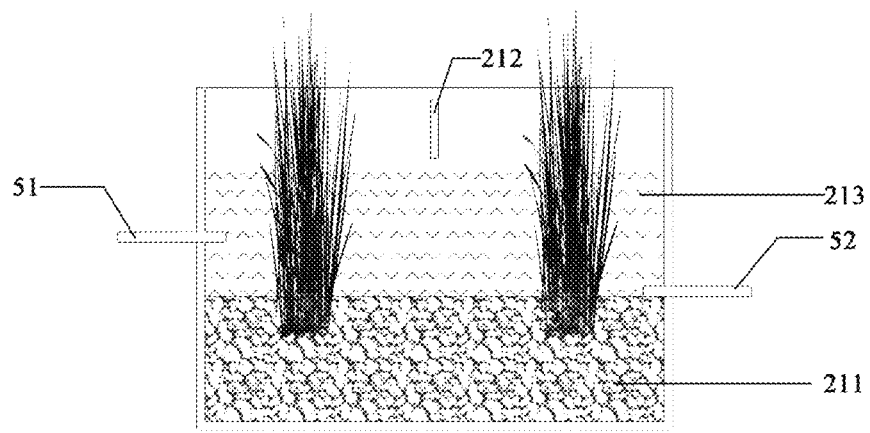
FIG. 3 is a profile structure schematic diagram of the planting unit of the simulation device of an example of the invention.

In some examples, as shown in FIG. 2, the simulation device of the present invention can be used to compare litter decomposition of different states (standing and lodging) of the same plant, to compare the difference of influences on water body under two states. The specific operation is as follows: collecting the litters of a planting unit in which plants can continue to grow upright in the planting pool, placing the collected litters horizontally on the substrate surface of another planting unit to simulate the lodging state, and monitoring the litter decomposition of different states of the same plant at the same time. Alternatively, different individuals with the same or similar growth of the same plant are placed in the planting pool, which is also available to control the different states of standing and lodging.

In the specific experimental operation, the planting density of the plant in the planting unit can be designed according to the specific requirements of the experiment.

Due to the complete simulation device of the present invention can highly simulate and restore the entire process of the influence of plant litters, especially wetland plant litters on water quality, in addition to being used for studying the influence of litter on water quality, the device of the present invention can be further used to sequentially remove the plant litters in the wetland water body according to the experimental result, thereby achieving the purpose of reducing polluted water.

The specific operation of removal is by manual removal, and the difference of influences of different wetland plants on water quality can be compared through the detection result of the influence of plant litter planted in the device on water quality. The influence of some wetland plants on water quality is great, and some is little, or some is fast and some is slow. Therefore, ifs available to remove in order according to the difference of influences, for example, the litters with large or fast impacts on the water body can be removed firstly, and the litters with small or slow impacts can be removed finally.

An important function of the simulation device of this invention is to study the result of the influence of different litters decomposition on water quality, and the obtained result, is applied to litter management of natural constructed wetland. If some plants litters have a greater impact, they can be removed at the end of growth.

If the monitoring results show that the plant litters in the decomposition stage will have a greater impact on water quality, which will cause "secondary pollution" to the water body, then in this case, it is necessary to remove the litters from the wetland.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All headings are for the convenience of the reader and should not be used to limit the meaning of the text that follows the heading, unless so specified.

As used herein and in the appended claims, the singular forms "a," "an," and "the" include plural referents unless the context clearly dictates otherwise. For example, "a" or "an" means "at least one" or "one or more."

The above examples are merely preferred examples of the present invention, in order to facilitate a better understanding of the present invention, and the scope of the present invention is not limited to the following examples, for example, the simulation device of the present invention is not limited to the study of the influence of wetland plant litter on water quality, but also be used for the study of litter of plants in addition to wetland plants which can produce litters and whose litters affect water quality, and the detection performance and effect equivalent to the above examples can be obtained, and will be no more repetition herein. In the meantime, the present invention is susceptible to various modifications and changes, and any modifications, equivalent replacement and improvements made in the spirit and scope of the present invention are intended to be included in the scope of the present invention.

The invention claimed is:

1. Simulation device for studying the influence of decomposition of plant litter on water quality, comprising a distributing reservoir, a planting pool and a discharge bay, and the distributing reservoir, the planting pool, and the discharge bay are connected successively through a first-level pipeline; the distributing reservoir is used for supplying water to the planting pool; the discharge bay is used for collecting wastewater discharged from the planting pool; the planting pool comprises at least one planting unit;

the planting unit is a container-like structure and used to hold a planting substrate and plant the plant on the planting substrate;

according to a direction of water flow, the first-level pipeline leading from the distributing reservoir to the planting pool is a first-level inlet pipeline, the pipeline leading from the planting pool to the discharge bay is a first-level outlet pipeline; each planting unit has a water inlet and a water outlet, and the water outlet of each planting unit is respectively connected to the first-level outlet pipeline through a second level outlet pipeline, and the water inlet of each planting unit is connected to the first-level inlet pipeline through a second level inlet pipeline, so that the respective planting units are arranged in the parallel arrangement.

2. The simulation device according to claim 1, wherein the planting pool comprises a plurality of planting units; the plurality of planting units are arranged in parallel arrangement, so that the water flowing out of the distributing reservoir can enter each planting unit respectively, and the wastewater in each planting unit can flow out separately and enter the discharge bay.

3. The simulation device according to claim 1, wherein the plurality of planting units are arranged in an array along arrangement direction of the first-level pipeline; the planting pool includes at least 1 array; inside the array, each planting unit through respective second level pipelines connecting with the first-level pipelines leading from the distributing reservoir to form the parallel arrangement.

4. The simulation device according to claim 3, wherein the planting pool comprises two of said arrays; according to a direction of water flow, the first-level inlet pipelines of two branches formed by a left and right branches of the first-level pipeline from the distributing reservoir enter the upstream part of two of said arrays respectively, and the first-level outlet pipelines of the two branches leading from the downstream part of the two arrays rejoin to form a first-level outlet pipeline which is connected to the discharge bay, in order to form the parallel arrangement.

5. The simulation device according claim 3, wherein the first-level pipeline and the second level pipeline are provided with on-off valves for controlling water in and out; a diameter of the first-level pipeline is larger than a diameter of the second level pipeline.

6. The simulation device according to claim 5, wherein both of the second level pipeline and the second level pipeline on the upstream and downstream part of the planting pool of the simulation device are provided with on-off valves.

7. The simulation device of claim 6, wherein an on-off valves is arranged on the location of the first level pipeline leading from the distributing reservoir of the simulation device which is near the water outlet of the distributing reservoir.

8. The simulation device according to claim 1, wherein the water inlet of the planting unit is parallel to or higher than the water outlet; the water outlet of the planting unit is disposed at a position parallel to or slightly lower than an upper surface of a planting substrate in the planting unit.

9. The simulation device according to claim 1, wherein a baffle is vertically disposed in the planting unit for preventing plants in the planting unit from falling down.

10. The simulation device according to claim 1, wherein the plant is a wetland plant; a planting substrate in the planting unit is a substrate suitable for the growth of the plant.

11. A simulation method for studying an influence of plant litter decomposition on water quality, characterized in that, the plant is planted in the planting unit of the planting pool of the simulation device of claim 1.

12. The simulation method according to claim 11, wherein after the plant is planted in the planting unit, the water in the distributing reservoir is discharged into the planting pool by controlling the flow of the water body by controlling on-off valves, and after a period of time changes of indictor in water are measured after decomposition of the plant litter in the planting pool.

13. The simulation method according to claim 11, wherein the plant is a wetland plant; different or identical wetland plants are planted between each planting unit.

* * * * *